United States Patent [19]

Odell

[11] 4,444,310

[45] Apr. 24, 1984

[54] SEGMENTED MULTI-PRODUCT PACKAGE ASSEMBLY

[75] Inventor: Robert Odell, Franklin Lakes, N.J.

[73] Assignee: Becton, Dickinson and Company, Paramus, N.J.

[21] Appl. No.: 401,794

[22] Filed: Jul. 26, 1982

[51] Int. Cl.³ .................. B65D 83/04; B65D 85/62; B65D 81/04

[52] U.S. Cl. ..................... 206/366; 206/363; 206/534.1; 206/539; 206/438; 206/471; 206/461; 206/526; 206/813; 206/815

[58] Field of Search ............... 206/363, 366, 534.1, 206/530, 534.2, 539, 438, 471, 461, 469, 813, 815, 820, 445, 526, 460; 229/43 R

[56] References Cited

U.S. PATENT DOCUMENTS

| | | | |
|---|---|---|---|
| 3,301,392 | 1/1967 | Regan, Jr. ............................ | 206/363 |
| 3,305,077 | 1/1967 | Greif et al. ........................... | 206/539 |
| 3,305,084 | 2/1967 | Higgins et al. ...................... | 206/366 |
| 3,454,210 | 7/1969 | Spiegel et al. ...................... | 229/43 R |
| 3,913,562 | 10/1975 | Moore et al. ....................... | 206/363 |
| 4,015,709 | 4/1977 | Millet ................................ | 206/526 X |

Primary Examiner—William T. Dixson, Jr.
Assistant Examiner—Brenda J. Ehrhardt
Attorney, Agent, or Firm—John L. Voellmicke

[57] ABSTRACT

A segmented multi-product package assembly contains articles such as hypodermic syringe tip caps. The package assembly includes a tray which contains a plurality of receptacles having open ends associated with an upper surface of the tray. These receptacles are arranged so that sealing areas on the upper surface lie between adjacent open ends. A cover is removably sealed to the sealing areas and covers the receptacles. The cover is partially removable from the tray to expose a selectable number of articles while the unused articles remain protected in sealed receptacles.

6 Claims, 8 Drawing Figures

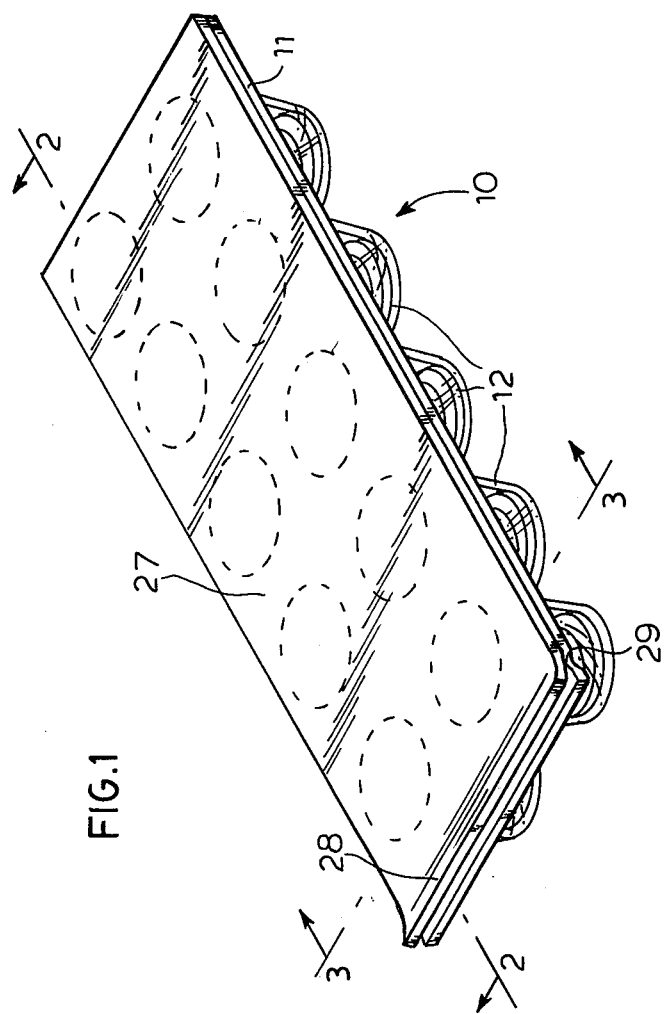

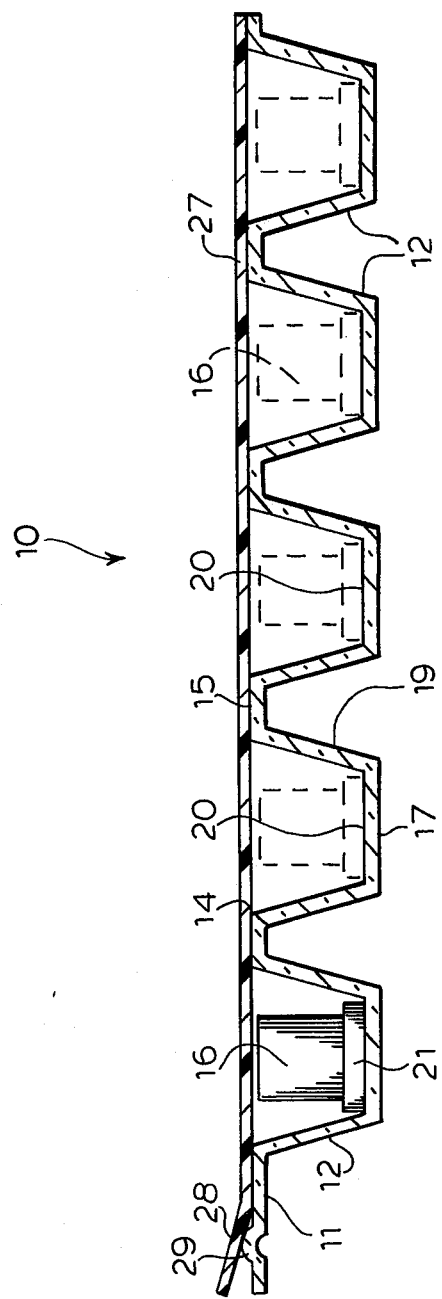

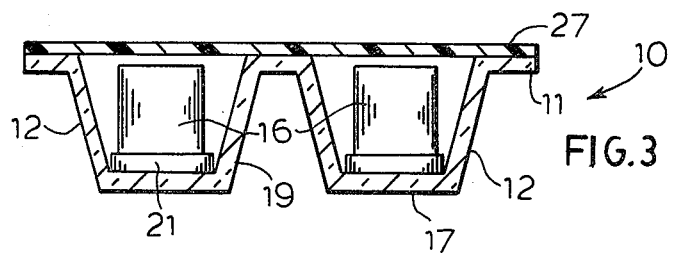
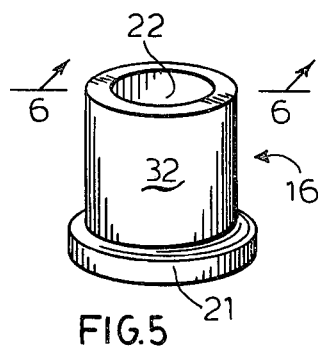
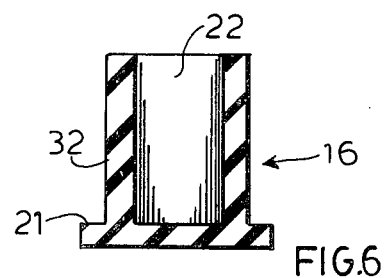
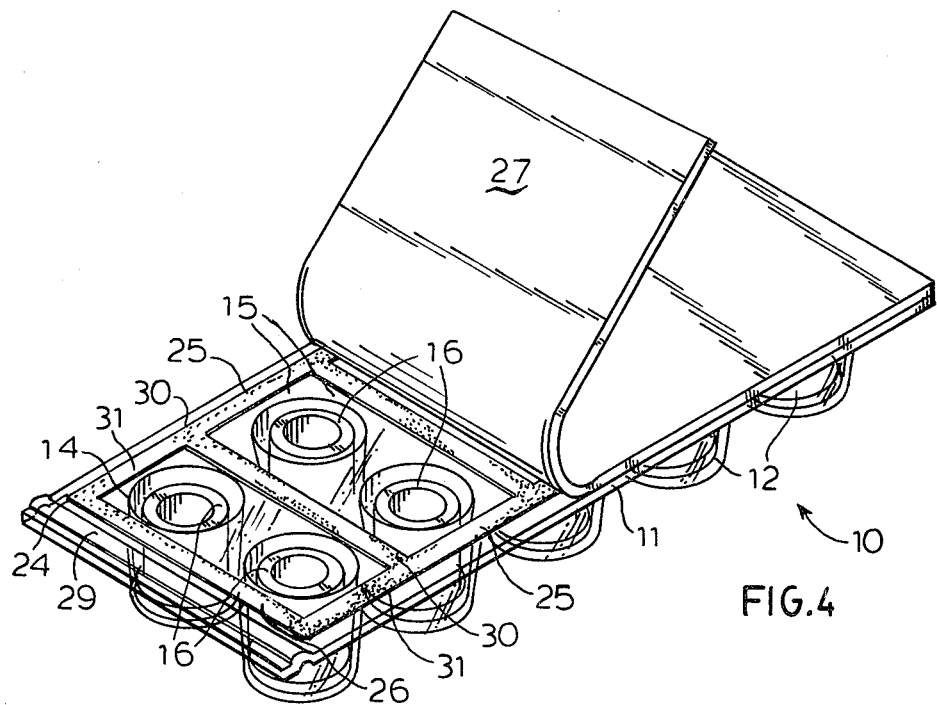

SEGMENTED MULTI-PRODUCT PACKAGE ASSEMBLY

FIELD OF THE INVENTION

The present invention relates to a segmented package assembly containing articles, and more particularly, concerns a segmented package assembly containing hypodermic syringe tip caps certain of which may be preselectably exposed for use while those that remain are protected in the package.

DESCRIPTION OF THE PRIOR ART

Articles such as hypodermic syringe tip caps are packaged in sterile containers. These tip caps are, for example, used in conjunction with hypodermic syringes in the preparation of prefilled syringe units. For instance, many hospitals employ drug distribution systems that require certain medications to be delivered to the nursing unit or floor in unit-of-use packages. Many injectable medications are not available commercially in unit-of-use form, therefore, these injectables must be prepared by the hospital pharmacy. This procedure usually takes place in a laminar flow hood where a pharmacist fills a quantity of syringes with medication from vials using readily available devices. After filling, the tip of the syringe is sealed with a tip cap and then the filled syringes are placed in a storage area to await delivery to the nursing unit or floor for administration of the medication to a patient.

Syringe tip caps are presently available in a container with a sealed lid. When the known and available container is opened the sterile field is broken and all of the tip caps contained therein must be used at that time or be discarded. Also, the tip caps are usually randomly oriented in this type of package so the technician often uses the tip of the filled syringe to topple the tip cap into the upright position so that the hypodermic syringe tip may be inserted into it. This procedure is undesirable since it may result in contamination of the syringe tip with particulate matter in the package and on the tip cap, and it may also result in the accidental depositing of medication from the syringe tip onto the exterior of the tip cap. Another known and available package holds the tip caps in proper orientation for syringe tip insertion but still exposes all tip caps when the package is opened. Again, this package requires disposal of the unused tip caps which are expensive components in the unit-of-use syringe assembly. Keeping unused tip caps, from a completely opened package, for later use creates the risk of contamination of the medication which is to be injected into the patient.

With the above mentioned deficiencies in mind, it is desired to provide a tip cap package assembly which can be selectively opened to expose only those tip caps which are needed at the time of use. It is further desired to provide a package assembly wherein the tip caps are contained in an orientation which allows direct syringe tip insertion into the tip cap.

SUMMARY OF THE INVENTION

The segmented package assembly of the present invention comprises a tray member which includes a plurality of receptacles. Each of the receptacles has an open end associated with an upper surface of the tray member and the receptacles are arranged so that sealing areas on the upper surface lie between adjacent open ends. Cover means is removably sealed to the sealing areas thus covering the receptacles which contain the articles. The cover means can be partially removed from the tray member to expose a selectable number of articles while the unused articles remain protected in sealed receptacles.

In a preferred embodiment of the present invention a tray contains receptacles which are disposed substantially periodically in at least one row along an upper surface of the tray. These receptacles preferably contain hypodermic syringe tip caps and are adapted to prevent the tip caps from toppling from their originally inserted position. The sealing area of the tray includes two longitudinal strips extending along the upper surface adjacent to the receptacles so that the receptacles are positioned between the longitudinal strips. A plurality of cross strips joins the longitudinal strips and extends transversely across the upper surface. A removably sealed flexible cover is sealed to the sealing areas and covers the receptacles. The cover can be partially removed from the tray to expose a selectable number of tip caps while the unused tip caps remain protected in sealed receptacles.

In another embodiment of the present invention a portion of the cover means is unsealed to the upper surface and a raised projection is provided on the upper surface to raise the cover means away from the tray in the unsealed area in order to facilitate initial removal of the cover means from the tray.

In accordance with the principles of the present invention, a number of advantages and objectives are attained. Primarily, the present invention improves a unit-of-use drug distribution system by providing a package assembly that allows the user to expose only the number of tip caps needed in the preparation of prefilled unit-of-use syringes. This advantage prevents the waste caused by existing packages which require that the user expose all tip caps at one time and discard those tip caps not used. Further, the present invention substantially diminishes the risk to the patient caused by using previously exposed, but not used, tip caps which can contaminate the injectable medication. The present invention not only provides the pre-determined number of tip caps needed for a specific use, but also provides them in an orientation conducive to easy engagement of the hypodermic syringe without further contamination of the syringe tip.

The present invention also provides a physical indication to the user, while peeling the cover from the tray, as to when at least one additional tip cap has been exposed for use. This physical indication is primarily a result of the shape of the sealing area which makes the force required to remove the cover greater when the cover is being removed from the area between the receptacles than when the cover is being removed from the area of the receptacles. This structure allows the user to perceive an increase in the force required when at least one additional tip cap is available for use.

BRIEF DESCRIPTION OF THE DRAWINGS

FIG. 1 is a perspective view of the preferred segmented package assembly of the present invention in sealed condition;

FIG. 2 is a cross-sectional view of the segmented package assembly of FIG. 1 taken along line 2—2;

FIG. 3 is a cross-sectional view of the segmented package assembly of FIG. 1 taken along line 3—3;

FIG. 4 is a perspective view of the segmented package assembly of FIG. 1 with the cover partially removed from the tray;

FIG. 5 is a perspective view of a typical syringe tip cap;

FIG. 6 is a cross-sectional view of the syringe tip cap of FIG. 5 taken along line 6—6;

DETAILED DESCRIPTION

Figure 7:
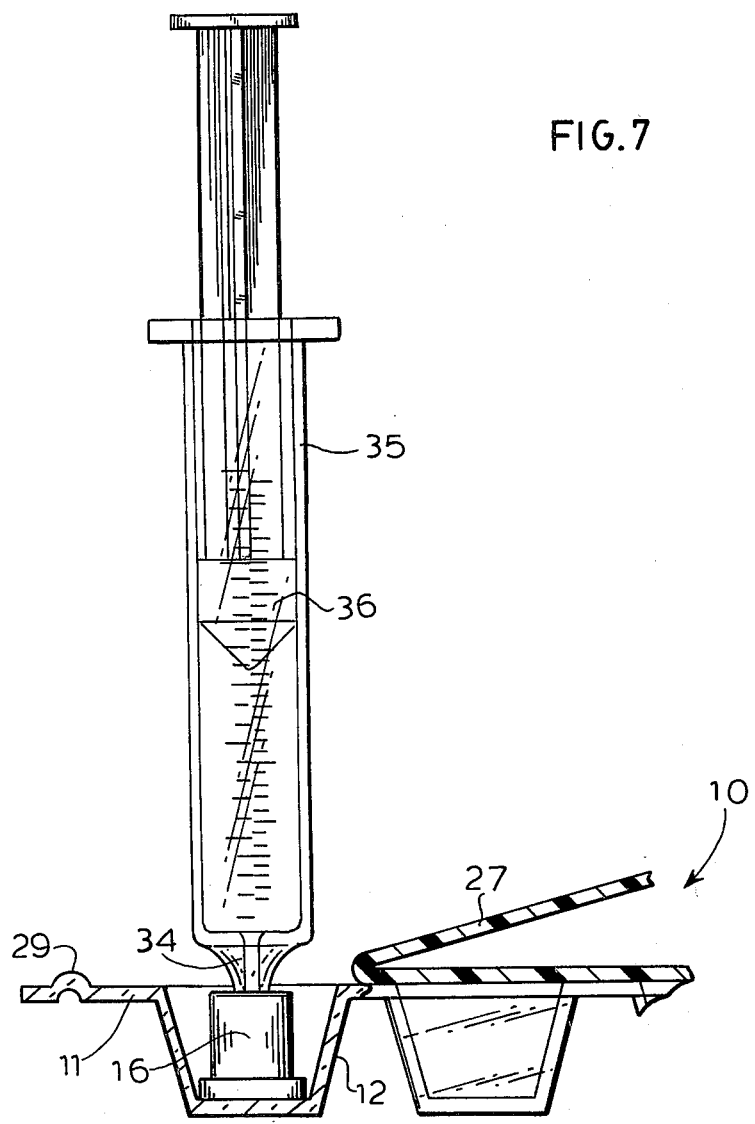
FIG. 7 is a side elevational view, partially in section, of the segmented package of FIG. 1 with the cover peeled back exposing a selective number of tip caps and with a hypodermic syringe tip inserted in one of the tip caps.

While this invention is satisfied by embodiments in many different forms, there is shown in the drawings and will herein be described in detail a preferred embodiment of the invention with the understanding that the present disclosure is to be considered as exemplary of the principles of the invention and is not intended to limit the invention to the embodiment illustrated. The scope of the invention will be measured by the appended claims and their equivalents.

Turning first to FIGS. 1 through 4, a segmented package assembly 10 includes a preferably oblong tray 11 having a plurality of receptacles 12. Each receptacle has an open end 14 at an upper surface 15 of the tray. Receptacles 12 are disposed substantially periodically in at least one row along upper surface 15. In the particular package assembly illustrated there are two rows with five receptacles in each row. It is understood that the number of rows and receptacles may be varied, and that random orientation of the receptacles also falls within the purview of the present invention. Each receptacle contains a tip cap 16 for sealing the tip of a hypodermic syringe. In the preferred embodiment each receptacle also has a flat bottom surface 17 and a substantially vertical cylindrical side wall 19. The flat bottom surfaces of the receptacles are in substantially the same plane as to provide a stable base for the package assembly. A sealing area 24 consists of longitudinal strips 25 and cross strips 26. In the illustrated embodiment sealing area 24 includes two substantially parallel longitudinal strips 25 extending along upper surface 15 and oriented substantially parallel to the longitudinal axis of oblong tray 11. Two rows of five receptacles each are positioned between and substantially parallel to the longitudinal strips. One receptacle in each row is positioned between the longitudinal strips and cross strips 26. The cross strips join the longitudinal strips and are preferably perpendicular to the longitudinal strips.

A flexible cover 27 is removably sealed to sealing area 24 and covers receptacles 12 and tip caps 16. Cover 27 is peeled away from tray 11 until the first receptacle in each row is exposed. In the illustrated embodiment two tip caps are then exposed for use and the remaining eight tip caps remain protected in sealed receptacles. This process may be repeated in subsequent procedures until all of the tip caps are exposed. When peeling cover 27 from the upper surface of the tray in an area 30, which lies between the receptacles, the length of seal being sheared is equal to the width of both longitudinal strips 25 plus the length of one cross strip 26. When peeling cover 27 from the tray in an area 31, which is over the receptacles, the length of seal being sheared is equal to the width of both longitudinal strips 25. Since the force required to peel the cover from the tray is proportional to the length of seal being sheared, the force required to remove the cover is greater when the cover is being removed from area 30, between the receptacles, than when the cover is being removed from area 31 over the receptacles. Therefore, the user perceives an increase in the force required to peel the cover from the tray when two additional tip caps have been exposed for use. It is understood that this force perception occurs when the cover is peeled from the tray generally in the direction of the longitudinal axis of the tray.

Referring to FIG. 2, a portion 28 of the flexible cover is unsealed to upper surface 15 and a raised projection 29 is provided on the upper surface of the tray to raise the cover away from the tray in the unsealed area in order to facilitate initial removal of the cover from the tray. Raised projection 29 can be placed at either or both ends of oblong tray 11 and is preferably formed in the same process that forms the receptacles. It is understood that many tray shapes are possible as long as the flexible cover joins the upper surface in the sealing area.

Referring now to FIGS. 5 and 6, tip cap 16, which is representative of those which are known and available, consists of a cylindrical body 32 with a flanged base 21 and a recess 22 for accepting and sealing the tip of a hypodermic syringe.

As seen in the drawings each receptacle 12 is adapted to prevent the tip cap from toppling from its inserted position. This is accomplished in the preferred embodiment by sizing the interior of the receptacle so that it closely contains the tip cap allowing only limited movement. In particular, the diameter of an interior flat bottom surface 20 of each receptacle is only slightly larger than the diameter of tip cap flanged base 21. A substantially vertical cylindrical side wall 19 extends upward from the interior flat bottom surface to form receptacle 12 which contains the tip cap so that it is not free to topple from its initial inserted position. It is understood that the concepts of this invention can be applied whenever the tip caps have different exterior geometries. The tip caps may also be held in their inserted position by mechanical interference provided by, for example, projections from the side walls of the receptacles, adhesive or other means of entrapment so long as the retention means does not prevent the withdrawal of the tip cap after insertion of the hypodermic syringe tip into the tip cap recess.

Figure 8:
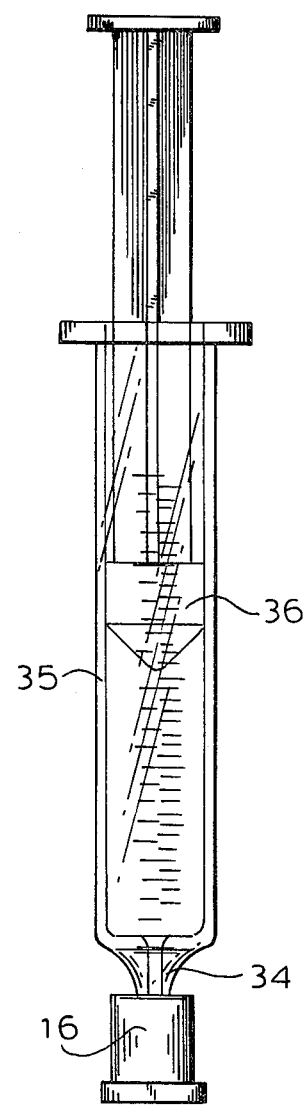
FIG. 8 is a side elevation view of a hypodermic syringe with a tip cap attached.

After a hypodermic syringe 35 has been filled with liquid medication, tip 34 of the syringe is normally sealed with tip cap 16. To accomplish this result, flexible cover 27 of the segmented package assembly is peeled away from tray 11 to expose the desired number of tip caps. The user will perceive an increase in the force required to peel the cover from the tray when, in the preferred embodiment, two additional tip caps have been exposed. The user will continue to peel the flexible cover from the tray until the desired number of tip caps are exposed for use. As illustrated in FIG. 7, the tip of the hypodermic syringe is urged into the recess of tip cap 16, while the tip cap is in the tray, to seal the contents of the syringe between the tip cap and syringe stopper 36. The syringe, with tip cap attached, is now removed as seen in FIG. 8 and the process is repeated until the desired number of syringes are filled and sealed with tip caps.

While many different materials may be utilized in fabricating the segmented package of the present invention, it is preferred that the tray be made of transparent, rigid plastic. Desirably, this plastic should be lightweight, but should resist being crushed under normal handling conditions.

The cover may be sealed to the tray by use of adhesives, heat sealing or other like means. The specific shape of the sealing areas may be achieved by selectively coating the cover or the tray with adhesive or heat sealable material, by using heat sealing dies in the shape of the desired heat sealing area, by providing a raised area on the tray in the shape of the desired heat sealing area or by other such means. It is preferred that the seal of the cover to the tray be sufficient to maintain the contents inside the package in clean, sterile condition. A fiber free cover is also desirable from this standpoint.

Thus there has been provided, in accordance with the present invention, a segmented multi-product package assembly which provides a pre-selectable number of syringe tip caps required by the user in an orientation conducive to easy engagement of the hypodermic syringe without further contamination of the syringe tip and which also provides physical indication, when peeling the cover from the tray, to notify the user when additional tip caps have been exposed.

What is claimed is:

1. A segmented package containing syringe tip caps comprising:

a tray having a plurality of receptacles therein, each of said receptacles terminating in an open end at an upper surface of said tray, said receptacles disposed substantially periodically in at least one row along said upper surface, said receptacles arranged so that a sealing area on said upper surface lies between adjacent open ends, said sealing area including two substantially parallel longitudinal strips extending along said upper surface adjacent to said receptacles, said receptacles being positioned between said longitudinal strips, and a plurality of cross strips joining said longitudinal strips, said cross strips extending transversely across said upper surface;

a plurality of syringe tip caps for sealing hypodermic syringe tips positioned in said receptacles; and cover means removably sealed to said sealing area and covering said receptacles, said cover means being partially removable from said tray to expose a selectable number of said tip caps, the unused tip caps adapted to remain protected in sealed receptacles.

2. The package of claim 1 wherein said receptacles are adapted to maintain the tip caps in their inserted position and prevent them from toppling.

3. A segmented package containing syringe tip caps comprising:

an oblong tray having a plurality of receptacles therein, each of said receptacles terminating in an open end at an upper surface of said tray, said receptacles disposed substantially periodically in at least one row along said upper surface, said receptacles arranged so that a sealing area on said upper surface lies between adjacent open ends in each row, each of said receptacles containing a tip cap for sealing a hypodermic syringe tip and adapted to prevent the tip cap from toppling from its inserted position, said sealing area including two substantially parallel longitudinal strips extending along said upper surface adjacent to said receptacles, said receptacles being positioned between said longitudinal strips, and a plurality of cross strips joining said longitudinal strips, said cross strips extending transversely across said upper surface; and cover means removably sealed to said sealing area and covering said receptacles, said cover means being partially removable from said tray to expose a selectable number of said tip caps, the unused tip caps adapted to remain protected in sealed receptacles.

4. The package of claims 1 or 3 wherein a portion of said cover means is unsealed to said upper surface in order to facilitate initial removal of said cover means from said tray.

5. The package of claim 4 wherein said upper surface further includes a raised projection raising said cover means away from said tray in the unsealed area.

6. The package of claims 1 or 3 wherein said receptacles are made of transparent, rigid plastic.

* * * * *